(12) United States Patent
Yundt-Pacheco

(10) Patent No.: US 6,938,026 B2
(45) Date of Patent: Aug. 30, 2005

(54) SYSTEM AND METHOD FOR IMPLEMENTING QUALITY CONTROL RULES FORMULATED IN ACCORDANCE WITH A QUALITY CONTROL RULE GRAMMAR

(75) Inventor: John Yundt-Pacheco, Fairview, TX (US)

(73) Assignee: Bio-Rad Laboratories, Inc., Hercules, CA (US)

(*) Notice: Subject to any disclaimer, the term of this patent is extended or adjusted under 35 U.S.C. 154(b) by 185 days.

(21) Appl. No.: 10/624,042

(22) Filed: Jul. 21, 2003

(65) Prior Publication Data
US 2005/0022103 A1 Jan. 27, 2005

(51) Int. Cl.$^7$ .............................................. G06F 17/00
(52) U.S. Cl. ....................................................... 706/47
(58) Field of Search .......................................... 706/47

(56) References Cited

U.S. PATENT DOCUMENTS

| | | | |
|---|---|---|---|
| 5,937,364 A | | 8/1999 | Westgard et al. ............. 702/83 |
| 6,446,045 B1 | * | 9/2002 | Stone et al. ................... 705/26 |
| 6,549,876 B1 | | 4/2003 | Yundt-Pacheco ............ 702/182 |
| 6,829,587 B2 | * | 12/2004 | Stone et al. ................... 705/26 |

* cited by examiner

Primary Examiner—George Davis
(74) Attorney, Agent, or Firm—Stinson Morrison Hecker LLP

(57) ABSTRACT

A system and method that enables the implementation of quality control rules formulated in accordance with a quality control rule grammar. The system comprises a storage device and a processor operable to maintain in the storage device a database identifying a plurality of laboratory tests and corresponding quality control rules. The processor is also operable to receive a quality control rule for a specified laboratory test, wherein the quality control rule is expressed in accordance with a quality control rule grammar. The processor is further operable to transfer the quality control rule to the database for storage in relation to the specified laboratory test. Various exemplary embodiments of the system and associated method are provided.

41 Claims, 3 Drawing Sheets

SYSTEM AND METHOD FOR IMPLEMENTING QUALITY CONTROL RULES FORMULATED IN ACCORDANCE WITH A QUALITY CONTROL RULE GRAMMAR

CROSS-REFERENCE TO RELATED APPLICATIONS

Not Applicable.

STATEMENT REGARDING FEDERALLY SPONSORED RESEARCH OR DEVELOPMENT

Not Applicable.

FIELD OF THE INVENTION

The present invention relates generally to laboratory testing services and, more particularly, to a system and method that enables the implementation of quality control rules formulated in accordance with a quality control rule grammar.

BACKGROUND OF THE INVENTION

Clinical laboratories use various types of quality control rules to identify performance issues with the laboratory instruments used to provide laboratory testing services. A common practice is to run a laboratory test on quality control specimens and evaluate the test results against one or more quality control rules to determine whether the test results are "in control" or "out of control." For example, if the quality control rule for a laboratory test is 1:3s (which means a range of 3 laboratory standard deviations around the laboratory mean) and the laboratory mean is 10 and the laboratory standard deviation is 1, then all test results falling between 7 and 13 would be accepted as "in control" and all other test results (e.g., 6 or 14) would be rejected as "out of control." If the test results are "in control," the laboratory instrument is deemed to be functioning properly and is thus suitable for testing actual patient specimens. On the other hand, the laboratory instrument is deemed to be malfunctioning if the test results are "out of control."

Because of the arithmetic complexity of quality control rules, laboratories use computer software to implement the quality control rules for all of the laboratory tests. Typically, the computer software includes a menu screen that allows a user to select one or more quality control rules (from a limited number of quality control rules) to be used in connection with each laboratory test. For example, a menu screen may provide the following available choices of quality control rules: 1:2s, 1:2.5s, 1:3s, 1:3.5s, 1:4s, 1:5s, 3:1s, 4:1s, 7T, 7x, 8x, 9x, 10x, and 12x.

As is known in the art, the 1:2s, 1:2.5s, 1:3s, 1:3.5s, 1:4s and 1:5s quality control rules mean that test results falling outside the range of 2 (or 2.5, 3, 3.5, 4 or 5) laboratory standard deviations around the laboratory mean would be rejected as "out of control." The 2:2s and (2 of 3):2s quality control rules mean that test results would be rejected as "out of control" when 2 (or 2 out of 3) consecutive test results are either lower than the laboratory mean minus 2 laboratory standard deviations, or, are higher than the laboratory mean plus 2 laboratory standard deviations. The R4s quality control rule means that test results would be rejected as "out of control" when there is a range exceeding 4 laboratory standard deviations between 2 test results.

Also, the 3:1s and 4:1s quality control rules mean that tests results would be rejected as "out of control" when there are 3 (or 4) test results on the same side of the laboratory mean plus 1 laboratory standard deviation. The 7T quality control rule means that test results would be rejected as "out of control" when there is a 7 point trend (either up or down) of the test results. Finally, the 7x, 8x, 9x, 10x, and 12x quality control rules mean that test results would be rejected as "out of control" when there are 7 (or 8, 9, 10 or 12) consecutive test results on the same side of the laboratory mean.

It can be appreciated that the available choices of quality control rules provided on the menu screen (e.g., 1:2s, 1:2.5s, 1:3s, 1:3.5s, 1:4s, 1:5s, 3:1s, 4:1s, 7T, 7x, 8x, 9x, 10x, and 12x) are very discrete and fairly limited. For example, a user cannot select a 1:2.75s quality control rule or a 5:1s quality control rule for a laboratory test because those quality control rules are not offered or implemented. Thus, the user's only option is to select the best of the available quality control rules for a particular laboratory test.

BRIEF SUMMARY OF THE INVENTION

The present invention is directed to a system and method that enables the implementation of quality control rules formulated in accordance with a quality control rule grammar such that the number of available quality control rules is significantly increased.

In an exemplary embodiment, the system includes a plurality of workstations and a server that operate in a client-server environment. The server includes a storage device and a processor operable to maintain in the storage device a database that identifies various sets of relational data, including laboratory tests/test results, laboratory tests/internal laboratory statistical data, laboratory tests/group statistical summary data, and laboratory tests/quality control rules.

Each of the workstations includes a processor operable to receive a quality control rule formulated in accordance with a quality control rule grammar. The quality control rule may comprise an expression formed of a plurality of tokens, such as an integer, a number, a points term, a statistic, a unary operator, an infix operator, a logical operator, and an inequality operator. Each processor is preferably operable to compile the received quality control rule to an intermediate code (such as using lexical analysis, syntactical analysis and semantic analysis) to thereby expedite the execution of the quality control rule at a later time. Finally, each processor is operable to transfer the quality control rule to the server database (preferably in both source code form and intermediate code form) for storage in relation to the appropriate laboratory test.

In another exemplary embodiment, the system includes a single workstation that operates in a single-user environment. The workstation includes a storage device and a processor operable to maintain in the storage device a database that identifies the various sets of relational data. The processor is also operable to receive a quality control rule formulated in accordance with a quality control rule grammar, compile the received quality control rule to an intermediate code, and transfer the quality control rule to the database for storage in relation to the appropriate laboratory test.

In yet another exemplary embodiment, the system includes a plurality of workstations and a server that operate in a Web-server environment. The server includes a storage device and a processor operable to maintain in the storage device a database that identifies the various sets of relational data. The processor is also operable to receive a quality control rule formulated in accordance with a quality control rule grammar (entered via one of the workstations), compile the received quality control rule to an intermediate code, and transfer the quality control rule to the database for storage in relation to the appropriate laboratory test.

The present invention will be better understood from the following detailed description of the invention, read in connection with the drawings as hereinafter described.

DETAILED DESCRIPTION OF THE INVENTION

The present invention is directed to a system and method that enables the implementation of quality control rules formulated in accordance with a quality control rule grammar.

Figure 1:
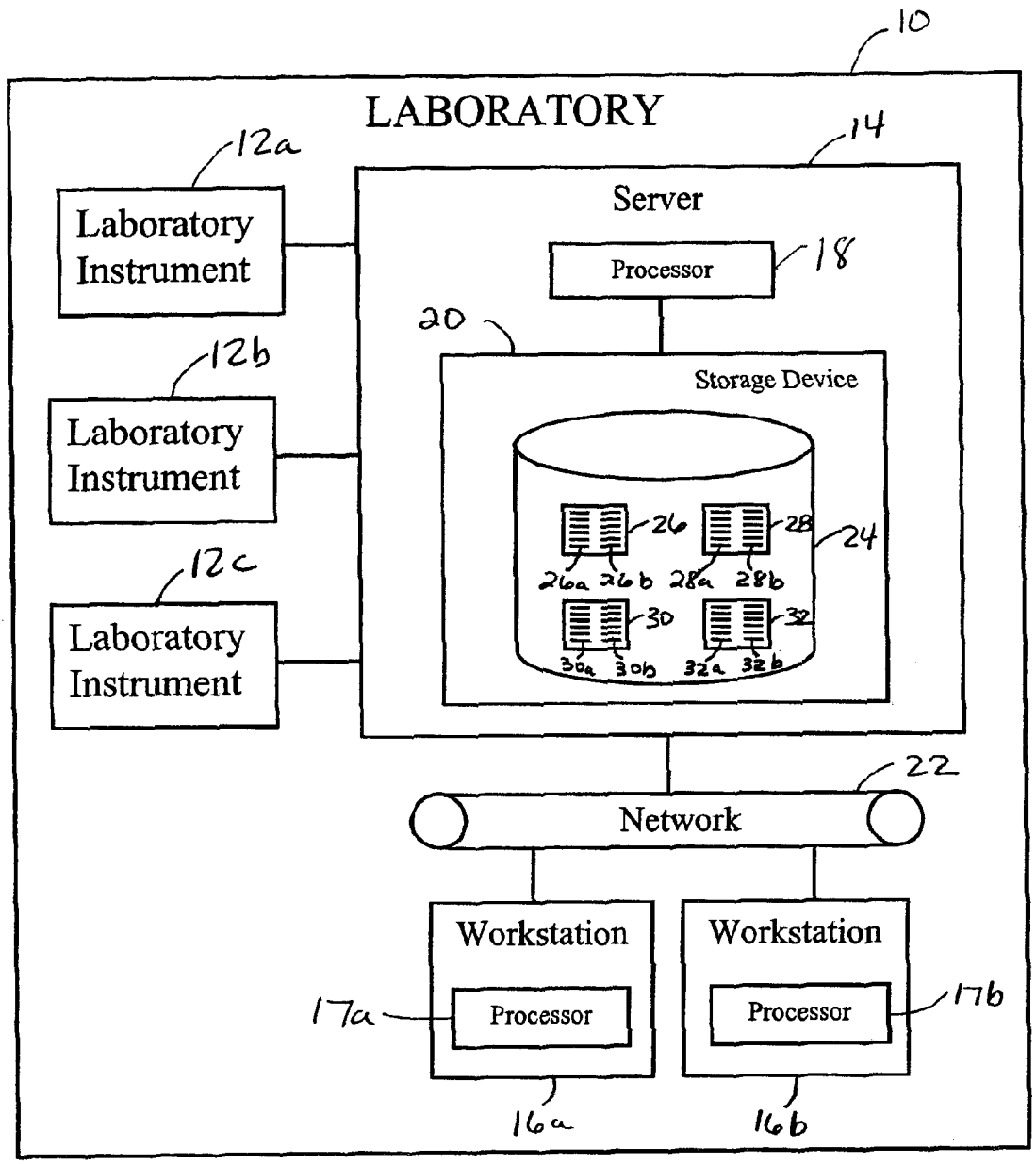
FIG. 1 is a block diagram of a system for implementing quality control rules formulated in accordance with a quality control rule grammar, in accordance with an exemplary embodiment of the present invention.

Referring to FIG. 1, an exemplary embodiment of a system in accordance with the present invention is depicted as a laboratory 10. Laboratory 10 includes one or more laboratory instruments 12a, 12b, and 12c connected to a server 14, which is in turn connected to one or more workstations 16a and 16b used by laboratory workers. While laboratory instruments 12a, 12b and 12c, server 14 and workstations 16a and 16b are shown as being co-located together within the same laboratory, it should be understood that one or more of these system elements could be located at a remote location (with suitable connections to the other system elements).

As is known in the art, laboratory instruments 12a, 12b and 12c may be utilized to perform a variety of different laboratory tests on quality control specimens prior to testing actual patient specimens. Laboratory instruments 12a, 12b and 12c may include identical instruments from the same manufacturer, different instruments from the same manufacturer, or different instruments from a variety of manufacturers. Examples of such laboratory instruments include the Olympus AU2700, the Abbott CELL-DYN 1700, the Vitros 950, the DPC Immulite 2000, the Bayer Rapidpoint 400, and the Dade Behring PFA 100. Of course, other types of laboratory instruments could also be used. Although three laboratory instruments have been shown in FIG. 1 for ease of illustration, it should be understood that laboratory 10 may include any number of laboratory instruments that are required for the provision of laboratory testing services. Typically, each of laboratory instruments 12a, 12b and 12c is connected to server 14 via an RS-232 serial connection, although other types of connections could also be used.

Workstations 16a and 16b each comprise a computing system, such as a personal computer or a character terminal. Each of workstations 16a and 16b includes a processor 17a and 17b that is operable to execute computer-readable instructions stored on a computer-readable medium to thereby perform certain processes of the invention, as will be described in greater detail hereinbelow. The computer-readable instructions executed by processors 17a and 17b may be coded using the Delphi programming language, although other programming languages could also be used, such as C, C++, Visual Basic, Java, Smalltalk, Eiffle, PERL and FORTRAN. The computer-readable medium may include any type of computer memory, such as floppy disks, conventional hard disks, CD-ROMS, Flash ROMS, non-volatile ROM and RAM. Although two workstations 16a and 16b have been shown in FIG. 1 for ease of illustration, it should be understood that laboratory 10 may include any number of workstations that are required for the provision of laboratory testing services.

Server 14 comprises a computing system that includes a processor 18 and a storage device 20. Examples of well-known computing systems that are suitable for use with the present invention include server computers, multiprocessor computers and mainframe computers, although other computing systems could also be used. Processor 18 is operable to execute computer-readable instructions stored on a computer-readable medium to thereby perform various processes of the present invention, as will be described in greater detail hereinbelow. The computer-readable instructions executed by processor 18 may be coded using the Delphi programming language, although other programming languages could also be used, such as C, C++, Visual Basic, Java, Smalltalk, Eiffle, PERL and FORTRAN. The computer-readable medium may include any type of computer memory, such as floppy disks, conventional hard disks, CD-ROMS, Flash ROMS, nonvolatile ROM and RAM.

In the illustrated example, workstations 16a and 16b and server 14 operate in a client-server environment, wherein each of workstations 16a and 16b operates as the "client" and server 14 operates as the "server." Workstations 16a and 16b communicate with server 14 via a communication network 22, such as an Ethernet network, a token ring network, or any other type of local area network or wide area network. Of course, other types of communication networks could also be used.

Referring still to FIG. 1, processor 18 of server 14 is operable to maintain in storage device 20 a database 24 that identifies various sets of relational data, including laboratory tests/test results, laboratory tests/internal laboratory statistical data, laboratory tests/group statistical summary data, and laboratory tests/quality control rules. Each set of relational data is preferably maintained in a separate table within database 24, although other database configurations could also be used. Server 14 may include any relational database software that is suitable for maintaining the various sets of relational data in storage device 20.

A first set of relational data 26 maintained within database 24 comprises a plurality of laboratory tests 26a and the test results 26b corresponding to each of the laboratory tests 16a. The test results 26b for each of the laboratory tests 26a consist of a collection of test results that have been obtained from laboratory instruments 12a, 12b and 12c during the internal testing of quality control specimens within laboratory 10. The first set of relational data will hereinafter be referred to as the "laboratory tests/test results table 26."

A second set of relational data 28 maintained within database 24 comprises a plurality of laboratory tests 28a (preferably the same as laboratory tests 26a) and the internal laboratory statistical data 28b corresponding to each of the laboratory tests 28a. The internal laboratory statistical data 28b consists of the statistical data derived from the test results 26b stored within laboratory tests/test results table 26. As such, the internal laboratory statistical data 28b is based solely on the test results originating from laboratory 10. The second set of relational data will hereinafter referred to as the "laboratory tests/laboratory statistics table 28."

A third set of relational data 30 maintained within database 24 comprises a plurality of laboratory tests 30a (preferably the same as laboratory tests 26a and 28a) and the group statistical summary data 30b corresponding to each of the laboratory tests 30a. The group statistical summary data 30b consists of the statistical data generated by a central agency in accordance with an external quality control program. As such, the group statistical summary data 30b is based on test results collected from a plurality of participating laboratories (including laboratory 10). The third set of relational data will hereinafter be referred to as the "laboratory tests/group statistics table 30."

A fourth set of relational data 32 maintained within database 24 comprises a plurality of laboratory tests 32a (preferably the same as laboratory tests 26a, 28a and 30a) and the quality control rules 32b corresponding to each of the laboratory tests 32a. As will be described in greater detail hereinbelow, each of the quality control rules 32b consists of an expression that defines when test results should be accepted as "in control" or rejected as "out of control." Some quality control rules may be expressed solely as a function of the internal laboratory statistical data for laboratory 10, such as the laboratory mean, the laboratory standard deviation, and the laboratory coefficient of variation. Other quality control rules may be expressed solely as a function of the group statistical summary data generated by the central agency, such as the group mean, the group standard deviation, and the group coefficient of variation. Yet other quality control rules may be expressed as a function of both the internal laboratory statistical data for laboratory 10 and the group statistical summary data generated by the central agency. Still other quality control rules may be expressed relative to the standard deviation index or the coefficient of variation index. Of course, other types of quality control rules could also be implemented. The fourth set of relational data will hereinafter be referred to as the "laboratory tests/quality control rules table 32."

In accordance with the present invention, the quality control rules 32b of laboratory tests/quality control rules table 32 are each formulated in accordance with a quality control rule grammar so that a user can dynamically select the appropriate quality control rule for a specified laboratory test. In an exemplary embodiment, the quality control rule grammar is defined such that each quality control rule consists of a plurality of different tokens, such as an integer (i), a number (n), a points term, a statistic, an infix operator, an inequality operator, a logical operator and/or a unary operator. These tokens are defined as follows (wherein the symbol | denotes alternative definitions):

i→any positive integer (e.g., 1, 2, 3, etc.)
    n→any positive rational number (e.g., 1, 1.25, 1.5, etc.)
    <points term>→i|(i of i)
    <statistic>→LM|s|LCV|GM|GSD|GCV|SDI|CVI
    <infix operator>→+|−|/|%
    <inequality operator>→<|>
    <logical operator>→"|"| and
    <unary operator>→X|T|R
wherein:
    LM=laboratory mean
    s=laboratory standard deviation
    LCV=laboratory coefficient of variation
    GM=group mean
    GSD=group standard deviation
    GCV=group coefficient of variation
    SDI=standard deviation index
    CVI=coefficient of variation index
    X=same side of a point
    T=trend
    R=range A quality control rule may then be characterized as an inequality expression, a unary expression or a range expression (or a combination of two or more of such expressions), as follows:

<quality control rule>→<inequality expression>
    <quality control rule>→<unary expression>
    <quality control rule>→<range expression>
    <quality control rule>→<quality control rule><logical operator><quality control rule>
wherein such expressions may take one of the following forms:
    <inequality expression>→<expression><inequality operator><expression>
    <unary expression>→R<expression>
    <unary expression>→<points term>X
    <unary expression>→<points term>T
    <range expression>→<points term><expression>:<expression>
    <range expression>→<points term>:<expression>
    (note: no expression after the "<points term>" and before the ":" assumes the laboratory mean)
and wherein:
    <factor>→i|n|<statistic>|<expression>
    <expression>→<factor>
    <expression>→<factor><factor>
    <expression>→<factor><infix operator><factor>

It should be understood that multiplication is implied when two factors are contiguous (e.g., <factor><factor>). Thus, a formal grammar is defined that may be utilized to formulate a quality control rule as desired for a specified laboratory test.

It can be appreciated that many different types of quality control rules may be formulated in accordance with the quality control rule grammar defined above. The following examples of formulated quality control rules are provided, along with an explanation of the meaning of such rules, to show the various types of quality control rules that may be implemented for different laboratory tests:

| | |
|---|---|
| 1:2s | a range of 2 laboratory standard deviations around the laboratory mean |
| 1:2.75s | a range of 2.75 laboratory standard deviations around the laboratory mean |
| 1GM:3LSD | a range of 3 laboratory standard deviations around the group mean |
| 1GM:(10% GM) | a range of 10% around the group mean |
| LCV < 5 | laboratory coefficient of variation is less than 5 |
| SDI < 2 | standard deviation index is less than 2 |
| R(4s) | a range of 4 laboratory standard deviations between 2 points |
| R(2GSD) | a range of 2 group standard deviations between 2 points |
| 11X | 11 points on the same side of the laboratory mean |
| 8T | a trend of 8 points in the same direction |
| 3LCV < GCV | group coefficient of variation is less than 3 laboratory coefficients of variation |
| 1GM:4 | a range of 4 about the group mean |
| 2GM:4 | 2 consecutive points out of range of 4 about the group mean |
| (2 of 3)GM:4 | 2 of 3 consecutive points out of range of 4 about the group mean |
| 1:3s|10X|R(4s) | either a point outside of 3 laboratory standard deviations from the laboratory mean or 10 points on the same side of the laboratory mean or a range of 4 laboratory standard deviations between points |

It should be understood that the quality control rule grammar defined above is merely an example of a formal grammar that may be utilized to implement a wide set of quality control rules for laboratory tests. Thus, one skilled in the art will understand that many different formal grammars could be defined in accordance with the present invention.

Referring still to FIG. 1, each of processors 17a and 17b of workstations 16a and 16b is operable to receive a quality control rule for a specified laboratory test, wherein the quality control rule is formulated in accordance with the quality control rule grammar. In one example, a user may formulate the quality control rule and then type the formulated quality control rule directly into one of workstations 16a and 16b. Each of processors 17a and 17b is then operable to receive the quality control rule in response to such direct input. In another example, a user may formulate the quality control rule and then add the formulated quality control rule to a quality control rule menu for subsequent selection by a user on one of workstations 16a and 16b. Each of processors 17a and 17b is then operable to receive the quality control rule in response to a user selection of the quality control rule from the quality control rule menu. Of course, it should be understood that the quality control rule menu may provide a wide variety of pre-defined quality control rules for possible user selection, while still allowing a user to directly input a different quality control rule that is not available on the quality control rule menu.

Upon receipt of the formulated quality control rule, each of processors 17a and 17b is preferably operable to compile the quality control rule to an intermediate code so as to expedite subsequent execution of the quality control rule by processor 18 of server 14 (which will be described further hereinbelow). As is known in the art, the quality control rule may be compiled using lexical analysis (which parses the quality control rule into separate tokens), syntactical analysis (which builds the parsed tokens into a parse tree) and semantic analysis (which applies any necessary transformations to the data). Of course, other compilation methods could also be used. Each of processors 17a and 17b is then operable to transfer the quality control rule (preferably in both source code form and intermediate code form) to server 14 for storage in relation to the specified laboratory test within laboratory tests/quality control rules table 32 of database 24.

It should be understood that each of processors 17a and 17b is operable to receive a formulated quality control rule, compile the quality control rule, and transfer the quality control rule to server 14 for a plurality of laboratory tests.

Finally, processor 18 of server 14 is operable to evaluate test results received from laboratory instruments 12a, 12b and 12c to determine whether the test results should be accepted as "in control" or rejected as "out of control." To do so, processor 18 is operable to execute the appropriate quality control rule stored within laboratory tests/quality control rules table 32 (applying the appropriate statistical data from laboratory tests/laboratory statistics table 28 and/or the appropriate laboratory tests/group statistics table 30). Processor 18 is then operable to evaluate the test results against the executed control rules to determine whether all of the test results are "in control" (whereby the laboratory instruments are deemed to be functioning properly) or whether one or more of the test results are "out of control" (whereby one or more of the laboratory instruments are deemed to be malfunctioning).

While the present invention has been described and illustrated hereinabove with respect to server 14 and workstations 16a and 16b that operate in a client-server environment, one skilled in the art will appreciate that the invention could also be applies to other types of environments.

For example, in another exemplary embodiment, the system includes a single workstation that operates in a single-user environment. The workstation includes a storage device and a processor operable to perform all of the functions performed by processors 17a and 17b and processor 18 described above. That is, the processor is operable to maintain in the storage device a database that identifies various sets of relational data, receive a quality control rule formulated in accordance with a quality control rule grammar, compile the received quality control rule to an intermediate code, and transfer the quality control rule to the database for storage in relation to the appropriate laboratory test.

In yet another exemplary embodiment, the system includes a plurality of workstations and a server that operate in a Web-server environment. The server includes a storage device and a processor operable to perform all of the functions performed by processors 17a and 17b and processor 18 described above. That is, the processor is operable to maintain in the storage device a database that identifies various sets of relational data, receive a quality control rule formulated in accordance with a quality control rule grammar (entered via one of the workstations), compile the received quality control rule to an intermediate code, and transfer the quality control rule to the database for storage in relation to the appropriate laboratory test.

Thus, the invention can be applied to systems that operate in a client-server environment, a single-user environment, and a Web-server environment.

Figure 2A:
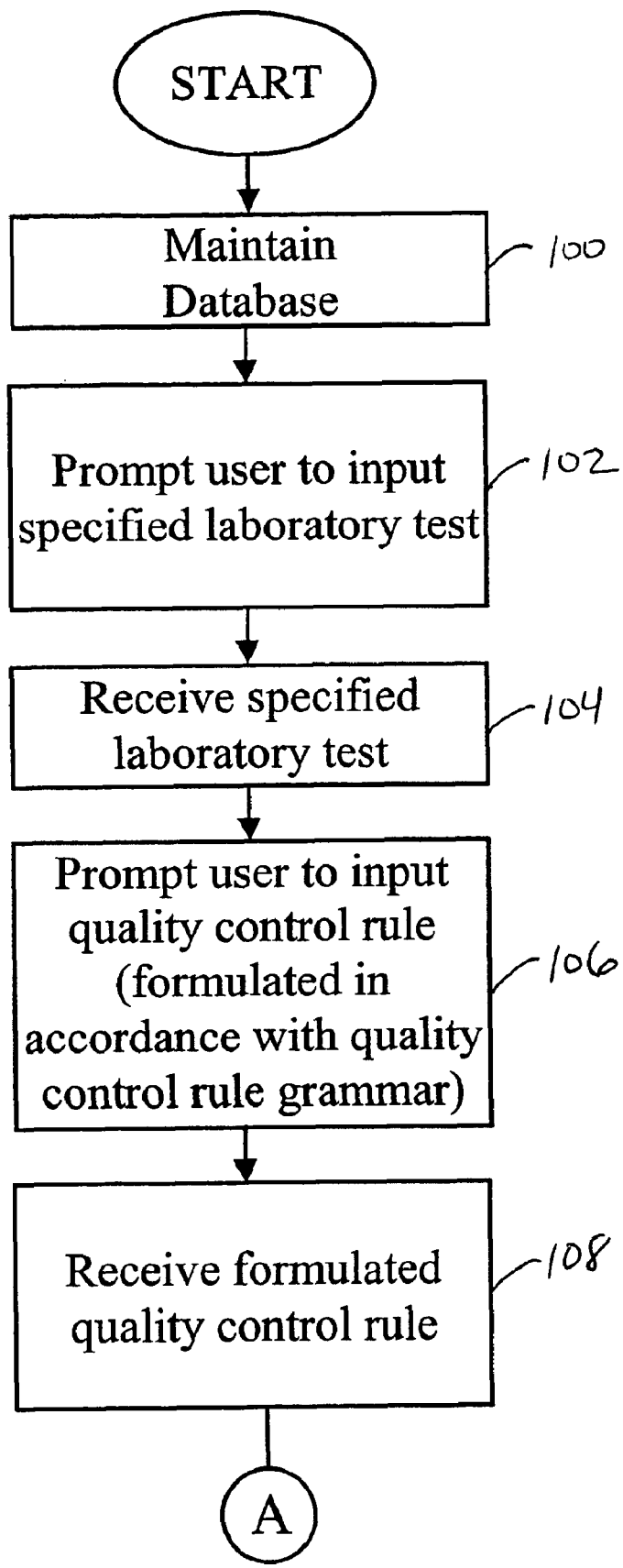
FIGS. 2A and 2B are flow charts of a method for implementing quality control rules formulated in accordance with a quality control rule grammar, in accordance with an exemplary embodiment of the present invention.
Figure 2B:
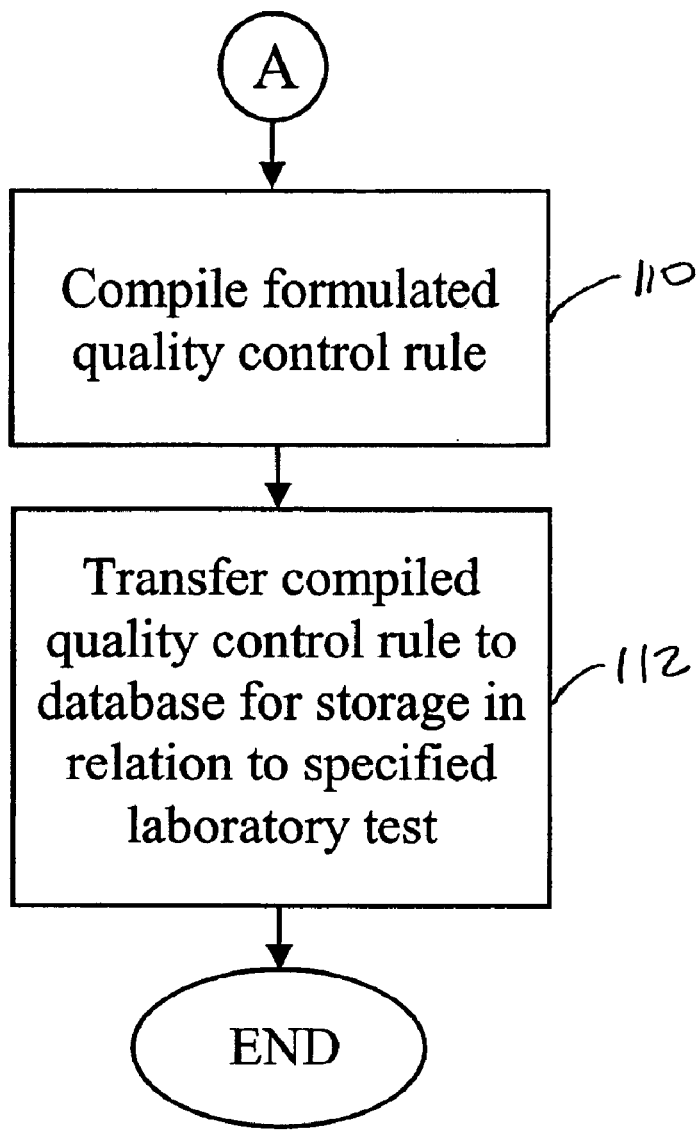

Turning now to FIGS. 2A and 2B, a flow diagram of a computerized method in accordance with an exemplary embodiment of the present invention is provided with reference to blocks 100–112. At block 100, a database is maintained that identifies various sets of relational data, including laboratory tests/test results, laboratory tests/internal laboratory statistical data, laboratory tests/group statistical summary data, and laboratory tests/quality control rules.

Then, at block 102, a user is prompted to input a specified laboratory test. In one example, the user may input the specified laboratory test by directly typing the specified laboratory test into a workstation. In another example, the user may select the specified laboratory test from a menu on the workstation. The specified laboratory test is then received (either via direct input or selection from a menu) at block 104.

Next, at block 106, a user is prompted to input a quality control rule for the specified laboratory test. In one example, a user may formulate the quality control rule and then type the formulated quality control rule directly into a workstation. In another example, a user may select a formulated quality control rule from a quality control rule menu on the workstation. In either case, the quality control rule is formulated in accordance with a quality control rule grammar (as discussed above). The formulated quality control rule is then received (either via direct input or selection from a quality control rule menu) at block 108.

Next, at block 110, the formulated quality control rule is compiled to an intermediate code so that subsequent execution of the quality control rule may be expedited. As is known in the art, the quality control rule may be compiled using lexical analysis, syntactical analysis and semantic analysis, although other compilation methods could also be used. Finally, at block 112, the quality control rule is transferred to the database (preferably in both source code form and object code form) for storage in relation to the specified laboratory test.

It will be apparent to one skilled in the art that the system and method of the present invention allows a user to dynamically formulate a quality control rule as desired for a particular laboratory test. By allowing the user to tailor the quality control rule to the particular laboratory test, certain test results may be accepted as "in control" that would otherwise have been considered erroneous under a traditional analysis (which limits the selection of quality control rules to a few discrete choices). Conversely, certain test results may be rejected as "out of control" that would otherwise have been considered valid under a traditional analysis. Thus, the use of a quality control rule grammar to allow the formulation of a wide set of quality control rules improves the quality of laboratory testing services.

While the present invention has been described and illustrated hereinabove with reference to exemplary embodiments, it should be understood that various modifications could be made to these embodiments without departing from the scope of the invention. Therefore, the invention is not to be limited to the specific systems and methods described and illustrated hereinabove, except insofar as such limitations are included in the following claims.

What is claimed and desired to be secured by Letters Patent is as follows:

1. A system for implementing grammar-based quality control rules for laboratory tests, comprising:
    a storage device;
    at least one processor operable to:
        maintain in said storage device a database identifying a plurality of laboratory tests and corresponding quality control rules;
        receive a quality control rule for a specified laboratory test, said quality control rule being expressed in accordance with a quality control rule grammar; and
        transfer said quality control rule to said database for storage in relation to said specified laboratory test.

2. The system of claim 1, wherein said processor is further operable to compile said quality control rule prior to transfer to said database.

3. The system of claim 2, wherein said quality control rule is compiled to an intermediate code.

4. The system of claim 2, wherein said quality control rule is compiled using lexical analysis, syntactical analysis and semantic analysis.

5. The system of claim 1, wherein said quality control rule is formulated by a user in accordance with said quality control rule grammar.

6. The system of claim 5, wherein said processor is operable to receive said quality control rule in response to a direct input of said quality control rule by said user.

7. The system of claim 5, wherein said quality control rule is added to a quality control rule menu for subsequent selection by one or more users.

8. The system of claim 7, wherein said processor is operable to receive said quality control rule in response to a user selection of said quality control rule from said quality control rule menu.

9. The system of claim 1, wherein said quality control rule comprises an expression formed of a plurality of tokens selected from the following group: an integer, a number, a points term, a statistic, a unary operator, an infix operator, a logical operator, an inequality operator, and combinations thereof.

10. The system of claim 9, wherein said statistic is selected from the following group: a laboratory mean, a group mean, a laboratory standard deviation, a group standard deviation, a laboratory coefficient of variation, a group coefficient of variation, a standard deviation index, and a coefficient of variation index.

11. The system of claim 1, wherein a first processor located in a server is operable to maintain said database in said storage device and a second processor located in a user workstation is operable to receive said quality control rule and transfer said quality control rule to said database.

12. The system of claim 1, wherein said processor is located in a server.

13. The system of claim 1, wherein said processor is located in a user workstation.

14. A computerized method of implementing grammar-based quality control rules for laboratory tests, comprising:
    maintaining a database identifying a plurality of laboratory tests and corresponding quality control rules;
    receiving a quality control rule for a specified laboratory test, said quality control rule being expressed in accordance with a quality control rule grammar; and
    transferring said quality control rule to said database for storage in relation to said specified laboratory test.

15. The computerized method of claim 14, further comprising compiling said quality control rule prior to transferring to said database.

16. The computerized method of claim 15, wherein said quality control rule is compiled to an intermediate code.

17. The computerized method of claim 15, wherein said quality control rule is compiled using lexical analysis, syntactical analysis and semantic analysis.

18. The computerized method of claim 14, wherein said quality control rule is formulated by a user in accordance with said quality control rule grammar.

19. The computerized method of claim 18, wherein said quality control rule is received in response to a direct input of said quality control rule by said user.

20. The computerized method of claim 18, wherein said quality control rule is added to a quality control rule menu for subsequent selection by one or more users.

21. The computerized method of claim 20, wherein said quality control rule is received in response to a user selection of said quality control rule from said quality control rule menu.

22. The computerized method of claim 14, wherein said quality control rule comprises an expression formed of a plurality of tokens selected from the following group: an integer, a number, a points term, a statistic, a unary operator, an infix operator, a logical operator, an inequality operator, and combinations thereof.

23. The computerized method of claim 22, wherein said statistic is selected from the following group: a laboratory mean, a group mean, a laboratory standard deviation, a group standard deviation, a laboratory coefficient of variation, a group coefficient of variation, a standard deviation index, and a coefficient of variation index.

24. A computer-readable medium having computer-executable instructions for performing a method of implementing grammar-based quality control rules for laboratory tests, said method comprising:
    maintaining a database identifying a plurality of laboratory tests and corresponding quality control rules;
    receiving a quality control rule for a specified laboratory test, said quality control rule being expressed in accordance with a quality control rule grammar; and
    transferring said quality control rule to said database for storage in relation to said specified laboratory test.

25. The computer-readable medium of claim 24, further comprising compiling said quality control rule prior to transferring to said database.

26. The computer-readable medium of claim 25, wherein said quality control rule is compiled to an intermediate code.

27. The computer-readable medium of claim 25, wherein said quality control rule is compiled using lexical analysis, syntactical analysis and semantic analysis.

28. The computer-readable medium of claim 24, wherein said quality control rule is formulated by a user in accordance with said quality control rule grammar.

29. The computer-readable medium of claim 28, wherein said quality control rule is received in response to a direct input of said quality control rule by said user.

30. The computer-readable medium of claim 28, wherein said quality control rule is added to a quality control rule menu for subsequent selection by one or more users.

31. The computer-readable medium of claim 30, wherein said quality control rule is received in response to a user selection of said quality control rule from said quality control rule menu.

32. The computer-readable medium of claim 24, wherein said quality control rule comprises an expression formed of a plurality of tokens selected from the following group: an integer, a number, a points term, a statistic, a unary operator, an infix operator, a logical operator, an inequality operator, and combinations thereof.

33. The computer-readable medium of claim 32, wherein said statistic is selected from the following group: a laboratory mean, a group mean, a laboratory standard deviation, a group standard deviation, a laboratory coefficient of variation, a group coefficient of variation, a standard deviation index, and a coefficient of variation index.

34. A system for implementing grammar-based quality control rules for laboratory tests, comprising:
    means for maintaining a database identifying a plurality of laboratory tests and corresponding quality control rules;
    means for receiving a quality control rule for a specified laboratory test, said quality control rule being expressed in accordance with a quality control rule grammar; and
    means for transferring said quality control rule to said database for storage in relation to said specified laboratory test.

35. The system of claim 34, further comprising means for compiling said quality control rule prior to transfer to said database.

36. The system of claim 34, wherein said quality control rule is formulated by a user in accordance with said quality control rule grammar.

37. The system of claim 34, wherein said quality control rule comprises an expression formed of a plurality of tokens selected from the following group: an integer, a number, a points term, a statistic, a unary operator, an infix operator, a logical operator, an inequality operator, and combinations thereof.

38. A computerized method of implementing grammar-based quality control rules for laboratory tests, comprising:
    maintaining a database identifying a plurality of laboratory tests and corresponding quality control rules;
    receiving a quality control rule for a specified laboratory test, said quality control rule being formulated by a user in accordance with a quality control rule grammar;
    compiling said quality control rule to an intermediate code using lexical analysis, syntactical analysis and semantic analysis; and
    transferring said converted quality control rule to said database for storage in relation to said specified laboratory test.

39. The computerized method of claim 38, wherein said quality control rule is received in response to a direct input of said quality control rule by said user.

40. The computerized method of claim 38, wherein said quality control rule is added to a quality control rule menu for subsequent selection by one or more users, and wherein said quality control rule is received in response to a user selection of said quality control rule from said quality control rule menu.

41. The computerized method of claim 38, wherein said quality control rule comprises an expression formed of a plurality of tokens selected from the following group: an integer, a number, a points term, a statistic, a unary operator, an infix operator, a logical operator, an inequality operator, and combinations thereof.

* * * * *